United States Patent [19]

Deinhammer et al.

[11] 4,187,237
[45] Feb. 5, 1980

[54] PROCESS FOR THE MANUFACTURE OF A FURANCARBOXYLIC ACID ANILIDE

[75] Inventors: Wolfgang Deinhammer; Rudolf Kaufmann, both of Burghausen; Hermann Braunling; Norman Haberle, both of Munich, all of Fed. Rep. of Germany

[73] Assignee: Consortium for Elektrochemische Industrie GmbH, Munich, Fed. Rep. of Germany

[21] Appl. No.: 480

[22] Filed: Jan. 2, 1979

[30] Foreign Application Priority Data

Jan. 5, 1978 [DE] Fed. Rep. of Germany ....... 2800504

[51] Int. Cl.² ............................................ C07D 307/68
[52] U.S. Cl. .................................................. 260/347.3
[58] Field of Search ...................................... 260/347.3

[56] References Cited

U.S. PATENT DOCUMENTS

| 3,978,091 | 8/1976 | Tsuchiya et al. | 260/347.3 |
| 4,094,990 | 6/1978 | Hubele | 260/347.3 |

OTHER PUBLICATIONS

Migrdichian "Organic Synthesis" vol. 2, (1957) p. 1439.
Dunlop et al. "The Furans" (1953) p. 561.

*Primary Examiner*—Alan L. Rotman
*Assistant Examiner*—R. W. Ramsuer
*Attorney, Agent, or Firm*—Allison C. Collard; Thomas M. Galgano

[57] ABSTRACT

A process for the manufacture of furancarboxylic acid anilides of the general formula

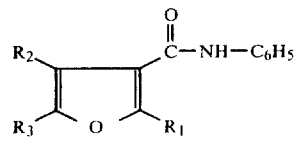

in which $R_1$ represents an aryl group or an alkyl group, $R_2$ and $R_3$ each represent an alkyl group or hydrogen, by a ring-closure reaction of a β-ketoester with an α-haloaldehyde or α-haloketone, in the presence of a stoichiometric amount of a halide-binding substance to form a furancarboxylic acid ester, and by subsequent anilidation, the reaction being performed in two stages, the ring-closure reaction being carried out in the presence of a mixture of alkaline earth metal carbonates and pyridine in a ratio of from 1000 to 5:1 Val, based on the hydrohalic acid liberated, at temperatures between 50° and 100° C.; and after separation in said second stage, the furancarboxylic ester is reacted while stirring with aniline in up to 20 times molecular excess, in the presence of equimolar amounts based on the furancarboxylic acid, of magnesium dianilide and/or aluminum trianilide in liquid phase or in suspension at temperatures between 20° and 180° C., under normal pressure. The furancarboxylic acid anilides have an outstanding pesticidal action.

5 Claims, No Drawings

PROCESS FOR THE MANUFACTURE OF A FURANCARBOXYLIC ACID ANILIDE

The invention relates to the production of a furancarboxylic acid anilide by a two-stage process in which a furancarboxylic acid ester is manufactured in a first stage and a furancarboxylic acid anilide is manufactured in a second stage.

According to Scott & Johnson, *J. Am. Chem. Soc.*, 54, 2549 (1932,) in the reaction of β-dicarbonyl compounds with α-halocarbonyls in the presence of equimolar amounts of pyridine, furan derivatives are obtained in yields of from 50 to 60%. No better yields are reported in the presence of ammonia, sodium carbonate, sodium acetate, triethylamine, sodium hydroxide or calcium hydroxide (E. Bisagni et al., *Bull. Soc. Chem. France* 1971 (11,) 4041 ff.). Finally, the production of 2-methylfuran-3-carboxylic acid ethyl ester proceeds according to DE-OS 20 06 472, without any information on yields, but with 3 moles of pyridine being used per mole of β-ketoester. All these processes have the disadvantage that either the yields are too low, or fairly large amounts of pyridine have to be used. The separation of fairly large amounts of pyridine from the reaction mixture and the working up of the waste liquors containing pyridine, always involves the use of a considerable amount of apparatus.

The anilidation of furancarboxylic acid esters by direct reaction with aniline does not produce industrially useful yields and purities. Anilidation with sodium anilide requires the industrially difficult handling of elemental sodium or of sodium hydride for the manufacture of sodium anilide.

A variation of the process in which carboxylic acid anilides are obtained from carboxylic acid esters and halomagnesium anilide, has the disadvantage that it has to be carried out by means of a Grignard reaction on an industrial scale. Moreover, for every mole of the reaction product, 2 moles of the Grignard compound are required.

It is therefore the object of the instant invention to provide a process for the manufacture of furancarboxylic acid anilides, in which better yields and purities are obtained in a first and second stage process. It is a further object of the present invention to facilitate the working up of the reaction product, as compared with conventional processes.

These objects are achieved, according to the instant invention, in a process for the manufacture of a furancarboxylic acid anilide of the general formula

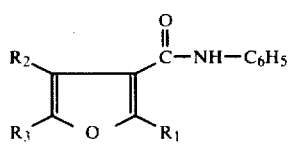

in which $R_1$ denotes an aryl group or an alkyl group, preferably a methyl group, $R_2$ and $R_3$ each denotes an alkyl group or hydrogen, preferably hydrogen, by a ring-closure reaction of a β-ketoester with an α-haloaldehyde or an α-haloketone, wherein halogen, preferably, stands for chlorine or bromine, the process being performed in a first stage in the present of a stoichiometric amount of a hydrogen halide-binding substance to form a furancarboxylic acid ester, and in a subsequent stage by anilidation. It is further characterized by carrying out the ring-closure reaction in the presence of a mixture of alkaline earth metal carbonates and, if desired, pyridine, in a ratio of from 1000 to 5:1 Val, preferably, from 200 to 20:1 Val, based on the hydrohalic acid liberated, at temperatures of between 50° and 100° C., preferably, from 65° to 80° C. and, after separation and distillation, reacting the furancarboxylic acid ester, while stirring, with aniline in up to 20 times molecular excess, in the presence of equimolar amounts, based on the furancarboxylic acid, of magnesium dianilide and/or aluminum trianilide, in liquid phase or in suspension, at temperatures of between 20° and 180° C., preferably, from 50° to 140° C., under normal pressure.

The good yields and the purity of the product obtained in both stages are surprising. It is not to be expected that of all the known acid-binding agents, alkaline earth metal carbonates would effect the desired improvement in the yields. The good course of the reaction of the first stage can be further improved by the addition of small amounts of pyridine. It has been found, however, that catalytic amounts of between 0.1 and 20 mole %, preferably, from 0.5 to 5 mole %, of pyridine, based on the β-dicarbonyl compounds used, accelerate the reaction sufficiently. Being familiar with the publication of Lazier and Atkins, *J. Am. Chem. Soc.* 46, 741 to 743, one skilled in the art would expect that during the reaction of the second reaction stage, the resulting magnesium alcoholate and aluminum alcoholate would produce an alkylated anilide, which would be difficult to remove. According to the instant invention, in the first reaction stage, alkaline earth metal carbonates are used as hydrogen halide-binding substances. For example, calcium carbonate is suitable, both in the form of precipitated calcium carbonate and in naturally occurring forms of calcium carbonate, such as, for example, limestone or chalk. Particularly suitable is naturally occurring dolomite, consisting of mixed crystals of calcium and magnesium carbonate. Advantageously, the alkaline earth metal carbonate is used in ground form. Suitable particle sizes for this purpose lie between 1 and 200μ. The alkaline earth metal carbonates are used in stoichiometric amounts, based on the hydrogen halide liberated. In certain circumstances, it may be necessary to use slightly larger amounts of alkaline earth metal carbonates, especially when using dolomite. The addition of pyridine in amounts of from 0.1 to 20 mole %, preferably, from 0.5 to 5 mole %, accelerates the reaction considerably. The use of molar amounts of pyridine, to say nothing of several times the molar amount, may be dispensed with.

In contrast to known processes, in the process according to the instant invention, it is not necessary additionally to use organic diluents, water, or dilute aqueous solutions of hydrogen halide-binding substances. As a result, there is a considerable reduction in the reaction volume by comparison with the customary method. The alkaline earth metal halides formed from the alkaline earth metal carbonates during the course of the reaction are readily soluble in water, and can therefore be removed with the aqueous phase, consisting of the water formed during the reaction or the water added after the reaction.

The reaction temperature is generally between 15° and 110° C. When the reaction temperatures are too low, however, the reaction proceeds slowly while, on the other hand, in the upper temperature range, by-products and secondary products are formed. The production of the furancarboxylic acid ester is carried out most advantageously at reaction temperatures of between 65° and 80° C. Working up the furancarboxylic acid ester is carried out in the usual manner, for example, by vacuum distillation.

As mentioned above, the process according to the instant invention produces higher yields than the known process. It is possible to dispense with the reclamation of expensive nitrogen bases.

The second reaction step, the reaction of the furancarboxylic acid ester with magnesium dianilide and/or aluminum trianilide, may be carried out in up to 20 times the molar excess of aniline, based on the carboxylic acid ester, under normal pressure and, if desired, in the presence of an inert organic diluent.

The anilides used according to the present invention are manufactured by heating a mixture of metal and aniline. The metal is used in the form of chips which have been activated, for example, in the presence of small amounts of a mercury salt. In the case of an excess of aniline, the metal anilide is formed in solution or in suspension.

The carboxylic acid ester is introduced, while stirring, into this solution or suspension of magnesium anilide and/or aluminum anilide. Owing to the heat of the reaction produced, during this operation it is sometimes necessary to carry out cooling. After the main reaction, it is advantageous to leave the reaction mixture at the reaction temperature for from 10 minutes to 24 hours. A suitable reaction temperature for the reaction, which is carried out under normal pressure, is from 20° to 180° C., but it is preferably carried out at from 50° to 140° C.

The amount of the carboxylic acid ester added is equimolar, based on the metal anilide. It is, of course, possible to add to the reaction mixture, as a diluent, an inert hydrocarbon, such as, for example, benzene toluene, xylene, cyclohexane, or ethers, such as diethyl ether, diisopropyl ether and dibutyl ether. Preferably, however, the reaction is carried out exclusively in excess aniline from the metal anilide formation. The separation of the excess aniline after the reaction, presents no difficulties. The greater part of the aniline is preferably distilled off, preferably at reduced pressure, owing to the fact that its boiling point is always lower compared with furancarboxylic acid anilides.

The remaining mixture may be worked up with water, producing alcohol, carboxylic acid anilide and metal hydroxide. Thereafter, the mixture is acidified with a mineral acid, preferably, hydrochloric acid or sulphuric acid, and the furancarboxylic acid anilide, which is insoluble in an aqueous medium, is filtered off. A variation of the work-up process consists of the anilide being dissolved, if desired, while heating, in organic solvents that are water-miscible with phase separation occurring, the solution being mixed with water, acidified with a mineral acid and the organic phase being worked up, after separation of the aqueous phase from the organic phase. The remaining residue may be recrystallized. However, the purity of the product is generally so high, that the product may at the same time be finished as a commercial product.

In the following Examples, the process of the present invention will be more fully described, and are given by way of illustration and not of limitation.

EXAMPLE 1

Production of 2-methylfuran-3-carboxylic acid methyl ester 58.055 kg (500 moles) of acetoacetic acid methyl ester are placed in a stirred autoclave and 22.5 kg (487.5 Val) of ground dolomite having a particle size of approximately 30μ, are stirred in. After adding 0.988 kg (12.5 moles) of pyridine, the mixture is heated to 70° C., and then 87.2 kg (500 moles) of 45% aqueous chloracetaldehyde solution are metered in over a period of approximately one hour. The reaction is maintained at 70° C. by cooling. Approximately four hours after the start of the reaction, slight heating must be carried out; after six to seven hours, the temperature is increased to from 75° to 80° C., whereupon heating is stopped, and stirring is continued for a while as the temperature drops. A total of 10 liters of concentrated hydrochloric acid is added in portions to the reaction mixture cooled to room temperature. After separation, the aqueous bottom layer is drained off and the organic layer is washed with 76 liters of water. In order to achieve better phase separation, approximately 2 kg of sodium chloride may be added. The organic phase is separated and distilled under reduced pressure. The yield of 2-methylfuran-3-carboxylic acid methyl ester is 53.6 kg, that is, 76.6% of the theoretical yield.

EXAMPLE 2

Production of 2-methyl-3-furancarboxylic acid anilide 18 g of aluminum granules were slightly etched with 2% aqueous mercury (I) chloride solution, then washed with water, methanol, toluene and aniline and, finally, refluxed with 700 ml of aniline for 10 hours, during which hydrogen escaped. 122 g of 2-methyl-3-furancarboxylic acid methyl ester were then introduced over a period of 10 minutes while stirring at 110° C., and stirring was continued for two hours at a temperature of from 110° to 120° C. The solution was then decanted from the unreacted aluminum (2.3 g,) while still hot, poured into water, acidified with 20% aqueous hydrochloric acid, and filtered. The precipitate of 2-methyl-3-furancarboxylic acid anilide, which had been washed neutral and dried, weight 172 g, that is, 94% of the theoretical yield.

EXAMPLE 3

2-methyl-3-furancarboxylic acid anilide 25 g of magnesium chips and 600 ml of aniline were heated under reflux for seven hours with the exclusion of atmospheric oxygen, during which hydrogen escaped. The mixture was then cooled to 120° C., and 140 g of 2-methylfuran-3-carboxylic acid methyl ester were added dropwise, while stirring over a period of 20 minutes. After stirring for two hours at 110° to 120° C., the excess aniline was distilled off in vacuo. The remaining melt was dissolved in 400 ml of toluene at 80° C. Then, 100 ml of water and, subsequently, 350 ml of 30% hydrochloric acid were added at 60° to 80° C. The aqueous bottom layer was separated, and may be further processed by alkalization to reclaim the aniline dissolved in the form of the hydrochloride.

The toluene solution was shaken twice at 60° to 80° C. with 5% hydrochloric acid, then shaken twice with water and, after the toluene had evaporated, a yield of 196 g of 2-methyl-3-furancarboxylic acid anilide of 98% purity was obtained.

Furancarboxylic acid anilides are known as active substances, having an outstanding pesticidal action. The new two-stage manufacturing process described above makes it possible to obtain better yields and high purity of the product, compared with the known production processes, as a result of which it is possible for the first time to produce the product on an industrially significant scale.

It will be obvious to those skilled in the art that other changes and variations can be made in carrying out the present invention, without departing from the spirit and scope thereof, as defined in the appended claims.

What is claimed is:

1. A process for the manufacture of furancarboxylic acid anilides of the general formula

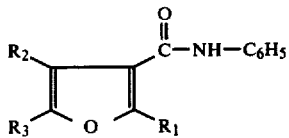

in which $R_1$ represents an aryl group or an alkyl group, $R_2$ and $R_3$ each represent an alkyl group or hydrogen, by a ring-closure reaction of a $\beta$-ketoester with an $\alpha$-haloaldehyde or alpha-haloketone, in the presence of a stoichiometric amount of a halide-binding substance, to form a furancarboxylic acid ester and by subsequent anilidation, the reaction being performed in two stages, the ring-closure reaction being carried out in the presence of a mixture of alkaline earth metal carbonates and pyridine in a ratio of from 1000 to 5:1 Val, based on the hydrohalic acid liberated, at temperatures between 50° and 100° C.; and, after separation in said second stage, the furancarboxylic ester is reacted while stirring with aniline in up to 20 times molecular excess, in the presence of equimolar amounts based on the furancarboxylic acid, of a member of the group consisting of magnesium dianilide, aluminum trianilide, and a mixture of both, in liquid phase or in suspension at temperatures between 20° and 180° C., under normal pressure.

2. The process according to claim 1, wherein the mixture of alkaline earth metal carbonates and pyridine is present in the ratio from 200 to 20:1 Val.

3. The process according to claim 1, wherein the ring-closure reaction is carried out at temperatures between 65° and 80° C.

4. The process according to claim 1, wherein the anilidation is carried out at temperatures between 50° and 140° C.

5. The process according to claim 1, wherein from one to two times the stoichiometric amount of the hydrogen halide-binding component is present.